US009435728B2

(12) United States Patent
Tsukii et al.

(10) Patent No.: US 9,435,728 B2
(45) Date of Patent: Sep. 6, 2016

(54) SAMPLE IDENTIFICATION/SORTING APPARATUS AND SAMPLE IDENTIFICATION/SORTING METHOD

(75) Inventors: Ken Tsukii, Tokyo (JP); Kenichi Kimura, Tokyo (JP); Toru Takahashi, Tokyo (JP); Jie Xu, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 636 days.

(21) Appl. No.: 13/342,233

(22) Filed: Jan. 3, 2012

(65) Prior Publication Data

US 2012/0097582 A1    Apr. 26, 2012

Related U.S. Application Data

(63) Continuation of application No. PCT/JP2010/056621, filed on Apr. 13, 2010.

(30) Foreign Application Priority Data

Dec. 25, 2009  (JP) ................................ 2009-294702
Apr. 12, 2010  (JP) ................................ 2010-091621

(51) Int. Cl.
*B07C 5/342* (2006.01)
*G01N 15/14* (2006.01)

(52) U.S. Cl.
CPC ...... *G01N 15/1459* (2013.01); *G01N 15/1404* (2013.01); *B01L 2300/0832* (2013.01); *B07C 5/342* (2013.01); *G01N 2015/149* (2013.01); *G01N 2015/1438* (2013.01)

(58) Field of Classification Search
CPC . B07C 5/02; B07C 5/342; B01L 2300/0819; B01L 2300/0829; B01L 2300/0832; G01N 33/4915; G01N 15/1404; G01N 15/1459; G01N 2015/149

USPC ............ 209/3.1, 44.2, 552, 576, 906, 932; 422/502–504
See application file for complete search history.

(56) References Cited

U.S. PATENT DOCUMENTS 3,710,933 A * 1/1973 Fulwyler et al. ............. 209/3.1
3,989,381 A * 11/1976 Fulwyler .................... 356/39
(Continued)

FOREIGN PATENT DOCUMENTS

| CN | 2748919 Y | 12/2005 |
|---|---|---|
| CN | 1973195 A | 5/2007 |

(Continued)

OTHER PUBLICATIONS

U.S. Appl. No. 13/561,941, filed Jul. 30, 2012, Takahashi, et al.
(Continued)

*Primary Examiner* — Joseph C Rodriguez
(74) *Attorney, Agent, or Firm* — Oblon, McClelland, Maier & Neustadt, L.L.P.

(57) ABSTRACT

A sample identification/sorting apparatus includes a sample storage portion that stores samples dispersed in a liquid, a flow cell having a flow path through which the liquid flows, and a sorting nozzle that has a flow path communicating with the flow path of the flow cell and dispenses a sorting solution including the sample, which is a target sample, to a culture plate. A difference between a flow direction of the liquid at an outlet of the sample storage portion and a flow direction of the liquid at a leading end of the sorting nozzle is less than 90 degrees.

22 Claims, 7 Drawing Sheets

(56) References Cited

U.S. PATENT DOCUMENTS

| | | | |
|---|---|---|---|
| 6,861,265 B1* | 3/2005 | den Engh | 436/177 |
| 6,994,218 B2* | 2/2006 | Kawano et al. | 209/210 |
| 7,355,696 B2* | 4/2008 | Mueth et al. | 356/244 |
| 7,392,908 B2* | 7/2008 | Frazier | 209/3.1 |
| 7,595,195 B2* | 9/2009 | Lee et al. | 436/52 |
| 7,746,466 B2* | 6/2010 | Godin et al. | 356/246 |
| 7,773,206 B2 | 8/2010 | Magnin et al. | |
| 7,987,022 B2* | 7/2011 | Handique et al. | 700/266 |
| 8,586,890 B2* | 11/2013 | Takahashi et al. | 209/577 |
| 2004/0260157 A1* | 12/2004 | Montes | 600/301 |
| 2005/0179156 A1* | 8/2005 | Carlson et al. | 264/40.1 |
| 2006/0141628 A1* | 6/2006 | Evans | 436/63 |
| 2006/0180517 A1* | 8/2006 | Frazier | 209/579 |
| 2008/0070311 A1* | 3/2008 | Li | 436/63 |
| 2008/0213821 A1* | 9/2008 | Liu et al. | 435/39 |
| 2008/0257072 A1 | 10/2008 | Takahashi et al. | |
| 2009/0079962 A1 | 3/2009 | Magnin et al. | |
| 2009/0107893 A1* | 4/2009 | Schembri et al. | 209/127.1 |
| 2010/0032349 A1* | 2/2010 | Shinoda | 209/132 |
| 2011/0089328 A1* | 4/2011 | Li | 250/364 |
| 2011/0143389 A1* | 6/2011 | Sharpe et al. | 435/29 |
| 2012/0152858 A1* | 6/2012 | Yang | 210/767 |
| 2012/0301869 A1* | 11/2012 | Evans | 435/2 |
| 2013/0288254 A1* | 10/2013 | Pollack et al. | 435/6.12 |

FOREIGN PATENT DOCUMENTS

| | | |
|---|---|---|
| CN | 101184985 A | 5/2008 |
| JP | 4-15540 | 1/1992 |
| JP | 9-288053 | 11/1997 |
| JP | 2005-127789 | 5/2005 |
| JP | 2008-164580 | 7/2008 |
| JP | 2009-2710 | 1/2009 |
| WO | WO 2005/103642 A1 | 11/2005 |

OTHER PUBLICATIONS

International Search Report issued Jul. 20, 2010 in Application No. PCT/JP2010/056621.

Office Action issued Apr. 8, 2011 in Japan Application No. 2010-550933 (With English Translation).

Tatsuo Yamashita, et al., Cell Technology, vol. 16, No. 10, 1997, pp. 1532-1541.

Combined Chinese Office Action and Search Report issued Sep. 29, 2012 in Chinese Patent Application No. 201080001871.5 (with English-language translation).

* cited by examiner

US 9,435,728 B2

SAMPLE IDENTIFICATION/SORTING APPARATUS AND SAMPLE IDENTIFICATION/SORTING METHOD

TECHNICAL FIELD

The present invention relates to a sample identification/sorting apparatus and a sample identification/sorting method that irradiate light onto a sample, which is a measurement target dispersed in a liquid flowing through a flow path, to measure optical information of the sample, determine whether the sample needs to be sorted on the basis of the optical information, and dispense a target sample, which is a sorting target, to a collection container on the basis of the determination result.

BACKGROUND ART

A sample identification/sorting apparatus (high-speed droplet charging-type cell sorter) has been proposed which makes a liquid having a sample (minute object), such as a cell, dispersed therein flow through a capillary tube and irradiates light from a light source to a liquid flow to measure the optical information (scattered light and fluorescent information) of the sample in the liquid flow, thereby identifying the sample (for example, see Non-patent Document 1). In the related art, after the sample is identified, a dispensing unit applies ultrasonic vibration to the liquid including a target sample to form droplets and a charge of, for example, several tens of volts is applied to the droplets. Then, several thousands of volts are applied from a polarizing plate to the droplets to divide the drop positions of the droplets into the positive electrode side and the negative electrode side, thereby dispensing the droplet to an arbitrary container (well) of the dispensing unit.

As such, in the high-speed droplet charging-type cell sorter according to the related art using ultrasonic waves, high voltage, and high water pressure, in the sorting process, since the target sample flies from the leading end of the nozzle to an arbitrary well of the plate by droplet charging. Therefore, there is a concern that a large physical damage (stress) will be applied to a living cell. In order to solve this problem, a sample dispensing/identification apparatus shown in FIG. 5, which is a cell sorter of a non-droplet cell sorting type, has been known (for example, see Patent Document 1). In the related art, the leading end of the nozzle is inserted into an arbitrary cell of the plate and the target sample is dispensed, thereby sorting the target sample, without changing a liquid including the target sample into droplets.

A sample dispensing/identification apparatus 100 includes a sample storage portion 101 that stores a sample dispersed in a liquid, a flow cell 102 having a flow path through which the liquid flows, a sorting nozzle 103, a collection container 104, an optical information measuring unit 105 that measures the optical information of the sample, and a tube 106 that introduces the liquid from the sample storage portion 101 to the flow cell 102.

CITATION LIST

Patent Document

Patent Document 1: Japanese Patent Application Laid-Open (JP-A) No. 2009-2710

Non-Patent Literature

Non-patent Literature 1: YAMASHITA Tatsuo, NIWA Shinichiro, Cell Technology, Vol. 16, No. 10, pp. 1532-1541, 1997

DISCLOSURE OF INVENTION

Problems to be Solved by the Invention

However, in the related art shown in FIG. 5, since there is a curved portion 107 in the tube 106 through which the sample dispersed in the liquid flows, a secondary flow 108 is generated toward the outside (the upper side of FIG. 6) of the tube 106 in the liquid flowing through the flow path of the curved portion 107, as shown in FIG. 6. In this case, there is a concern that the sample dispersed in the liquid will be moved toward the outside of the tube 106, contact the inner wall of the tube (the wall of the flow path) and be damaged.

As such, in the related art shown in FIG. 5, the damage of the sample, such as a living cell, is reduced, but it is necessary to further reduce the damage of weak cells including iPS cells.

The invention has been made in view of the above-mentioned problems of the related art, and an object of the invention is to provide a sample identification/sorting apparatus and a sample identification/sorting method capable of removing or reducing the cause of the damage of a sample, such as a living cell, in a sorting process to acquire a high-quality living cell.

Another object of the invention is to provide a sample identification/sorting apparatus and a sample identification/sorting method capable of improving the flexibility of the arrangement of a sample storage portion where a sample is dispersed in a liquid, and a flow cell that includes a flow path through which the liquid flows and an optical information measuring unit that measures the optical information of the sample.

Means for Solving the Problem

In order to solve the above-mentioned problems, according to a first aspect of the invention, there is provided a sample identification/sorting apparatus that irradiates light onto a sample, which is a measurement target dispersed in a liquid flowing through a flow path, to measure optical information of the sample, determines whether the sample needs to be sorted on the basis of the optical information, and sorts a target sample, which is a sorting target, to a collection container on the basis of the determination result. The sample identification/sorting apparatus includes: a sample storage portion that stores the sample dispersed in the liquid; a flow cell including a flow path through which the liquid flows and an optical information measuring unit that measures the optical information of the sample; and a sorting nozzle that includes a flow path communicating with the flow path of the flow cell and dispenses a sorting solution including the target sample to the collection container. A difference between the flow direction of the liquid at an outlet of the sample storage portion and the flow direction of the liquid at the leading end of the sorting nozzle is less than 90 degrees.

In the specification, the term "flow direction of the liquid" means the flow direction of the liquid along the central axis of the flow path. For example, the flow direction of the liquid does not include a variation in the wall of a flow path having a gap in a portion of the wall thereof or a variation in the wall of a flow path whose sectional shape is changed.

According to a second aspect of the invention, the sample identification/sorting apparatus according to the above-mentioned aspect may further include an introduction nozzle including a flow path that introduces the liquid from the sample storage portion to the flow path of the flow cell.

According to a third aspect of the invention, in the sample identification/sorting apparatus according to the above-mentioned aspect, the flow direction of the liquid in a flow path from the sample storage portion to the leading end of the sorting nozzle may be changed at an angle of less than 90 degrees.

According to a fourth aspect of the invention, in the sample identification/sorting apparatus according to the above-mentioned aspect, a flow path from the introduction nozzle to the leading end of the sorting nozzle may be a straight line.

In the specification, the "straight flow path" means a flow path having a straight central axis. For example, the "straight flow path" according to the invention includes a flow path having a gap in a portion of the wall thereof from the sample storage portion to the leading end of the sorting nozzle and a flow path whose sectional shape is changed as long as the central axes of the flow paths are a straight line.

The sorting nozzle is not limited to a cylindrical shape and is a flow-path-formed member having an opening at the end of a flow path immediately before the collection container. For example, the sorting nozzle has a rectangular parallelepiped shape and the leading end of the sorting nozzle is cut in a quadrangular pyramid shape with a size capable of being inserted into a well of, for example, a culture plate. Alternatively, when the sorting nozzle is vibrated to dispense a sorting solution including the sample at the leading end to an arbitrary well, the leading end of the sorting nozzle may have a size that is not inserted into a well of, for example, the culture plate.

According to a fifth aspect of the invention, in the sample identification/sorting apparatus according to the above-mentioned aspect, a flow path from the flow cell to the sorting nozzle may be a straight line.

According to a sixth aspect of the invention, in the sample identification/sorting apparatus according to the above-mentioned aspect, the sorting nozzle or the collection container may be moved to dispense the sorting solution to the collection container at the time when the target sample reaches the leading end of the sorting nozzle.

According to a seventh aspect of the invention, in the sample identification/sorting apparatus according to the above-mentioned aspect, the central axis of the straight flow path may be aligned with the vertical direction.

According to an eighth aspect of the invention, in the sample identification/sorting apparatus according to the above-mentioned aspect, a difference between the liquid level displacement direction of the liquid in the sample storage portion and the flow direction of the liquid having the sample dispersed therein in the flow path may be less than 90.

According to a ninth aspect of the invention, in the sample identification/sorting apparatus according to the above-mentioned aspect, the liquid level displacement direction of the liquid in the sample storage portion may be aligned with the flow direction of the liquid having the sample dispersed therein in the flow path.

According to a tenth aspect of the invention, in the sample identification/sorting apparatus according to the above-mentioned aspect, the collection container may be disposed below the leading end of the sorting nozzle in the vertical direction when the sample is sorted.

According to an eleventh aspect of the invention, in the sample identification/sorting apparatus according to the above-mentioned aspect, the liquid level displacement direction of the sample storage portion may be substantially vertical to the level of the liquid in the collection container.

The term "liquid level displacement direction in the collection container" means the liquid level displacement direction of a culture solution 51 (see FIG. 3) in a well when the culture plate having a plurality of wells arranged in, for example, a matrix is used as the collection container.

According to a twelfth aspect of the invention, in the sample identification/sorting apparatus according to the above-mentioned aspect, the sample storage portion may be arranged above the flow cell. The sample storage portion may be a cup-shaped container in which an opening portion through which the liquid is introduced is provided at an upper part and a discharge hole is provided in the bottom. The introduction nozzle including the flow path that introduces the liquid from the sample storage portion to the flow path of the flow cell may be provided between the sample storage portion and the flow cell.

The "cup-shaped container" has only the function of a container that stores the sample dispersed in the liquid.

According to a thirteenth aspect of the invention, in the sample identification/sorting apparatus according to the above-mentioned aspect, the sample storage portion may be arranged above the flow cell, and the sample storage portion may be a tubal container that includes an opening portion through which the liquid is introduced at an upper part thereof and has a function of storing the sample and the function of a flow path which forms a portion of the flow path and introduces the liquid to the flow path of the flow cell.

According to a fourteenth aspect of the invention, there is provided a sample identification/sorting apparatus that dispenses a target sample to a collection container. The sample identification/sorting apparatus includes: an optical information measuring unit that irradiates light onto a sample, which is a measurement target dispersed in a liquid flowing through a flow path, to measure optical information of the sample; a dispensing unit that dispenses a sorting solution including the target sample, which is a sorting target, to the collection container; a control unit that determines whether the sample needs to be sorted on the basis of the optical information and controls the driving of the dispensing unit on the basis of the determination result; a sample storage portion that stores the sample dispersed in the liquid; a flow cell including a flow path through which the liquid flows and the optical information measuring unit that measures the optical information of the sample; and a sorting nozzle that includes a flow path communicating with the flow path of the flow cell and dispenses the sorting solution including the target sample to the collection container. A difference between the flow direction of the liquid at an outlet of the sample storage portion and the flow direction of the liquid at the leading end of the sorting nozzle is less than 90 degrees.

According to a fifteenth aspect of the invention, in the sample identification/sorting apparatus according to the above-mentioned aspect, a flow path from the sample storage portion to the leading end of the sorting nozzle may be a straight line.

According to a sixteenth aspect of the invention, in the sample identification/sorting apparatus according to the above-mentioned aspect, the optical information measuring unit may include a plurality of measurement systems that are provided around the flow path at two or more different positions in the traveling direction of the sample and measure the optical information. The control unit may identify whether the sample is a target sample or a non-target sample on the basis of optical information obtained by the plurality of measurement systems, measure the flow rate of the target sample on the basis of a difference in the measurement time of the optical information obtained by the plurality of measurement systems and the gap between the measurement systems in the traveling direction of the sample, calculate the time when the target sample reaches the leading end of the sorting nozzle, and control the driving of the dispensing unit at the time when the target sample reaches the leading end of the sorting nozzle.

According to a seventeenth aspect of the invention, in the sample identification/sorting apparatus according to the above-mentioned aspect, a liquid that does not include the sample may flow through the flow path so as to surround the liquid having the sample dispersed therein.

According to an eighteenth aspect of the invention, there is provided a method of identifying and sorting a sample in a sample identification/sorting apparatus including a sample storage portion that stores the sample dispersed in a liquid, a flow cell including a flow path through which the liquid flows and an optical information measuring unit that measures the optical information of the sample, and a sorting nozzle that includes a flow path communicating with the flow path of the flow cell and dispenses a sorting solution including a target sample to a collection container. The method includes: irradiating light onto the sample, which is a measurement target dispersed in a liquid flowing through a flow path, to measure the optical information of the sample; determining whether the sample needs to be sorted on the basis of the optical information; and sorting the target sample, which is a sorting target, to the collection container on the basis of the determination result. A difference between the flow direction of the liquid at an outlet of the sample storage portion and the flow direction of the liquid at the leading end of the sorting nozzle is less than 90 degrees.

According to a nineteenth aspect of the invention, in the method of identifying and sorting a sample according to the above-mentioned aspect, the sample identification/sorting apparatus may further include an introduction nozzle including a flow path that introduces the liquid from the sample storage portion to the flow path of the flow cell, and the flow direction of the liquid in a flow path from the sample storage portion to the leading end of the sorting nozzle may be changed at an angle of less than 90 degrees.

According to a twentieth aspect of the invention, in the method of identifying and sorting a sample according to the above-mentioned aspect, the sample identification/sorting apparatus may further include an introduction nozzle including a flow path that introduces the liquid from the sample storage portion to the flow path of the flow cell, and a flow path from the introduction nozzle to the sorting nozzle may be a straight line.

According to a twenty-first aspect of the invention, in the method of identifying and sorting a sample according to the above-mentioned aspect, the sort solution may be dispensed to the collection container at the time when the target sample reaches the leading end of the straight flow path.

According to a twenty-second aspect of the invention, in the method of identifying and sorting a sample according to the above-mentioned aspect, the flow direction of the liquid having the sample dispersed therein in the flow path may be aligned with the vertical direction.

According to a twenty-third aspect of the invention, in the method of identifying and sorting a sample according to the above-mentioned aspect, the liquid level displacement direction of the liquid in the sample storage portion may be aligned with the flow direction of the liquid in the flow path.

According to a twenty-fourth aspect of the invention, in the method of identifying and sorting a sample according to the above-mentioned aspect, the sample dispersed in the liquid may be moved in a straight line from the sample storage portion and be sorted to the collection container.

According to a twenty-fifth aspect of the invention, in the sample identification/sorting apparatus according to the above-mentioned aspect, at least one bent portion may be provided in the flow path such that the flow direction of the liquid is changed at an angle of less than 90 degrees.

According to a twenty-sixth aspect of the invention, in the sample identification/sorting apparatus according to the above-mentioned aspect, the sort solution including the target sample at the leading end of the sorting nozzle may come into contact with a liquid in the collection container to be dispensed to the collection container, thereby sorting the target sample.

According to a twenty-seventh aspect of the invention, in the sample identification/sorting apparatus according to the above-mentioned aspect, the size of the flow path of the sorting nozzle may be equal to or greater than that of the flow path of the flow cell. Advantages of the Invention According to the invention, since there is no curved portion in the flow path from the sample storage portion to the leading end of the sorting nozzle, it is possible to reduce the collision risk of the sample, such as a living cell, with the wall of the flow path in the sorting process. Therefore, it is possible to remove or reduce the cause of the damage of the sample, such as a living cell, in the sorting process and thus acquire a high-quality living cell. In particular, it is possible to achieve a sample identification/sorting apparatus and a sample identification/sorting method which are effective in sorting weak cells including iPS cells.

According to the invention, even when there are restrictions in the arrangement of the sample storage portion where a sample is dispersed in a liquid, and the flow cell having a flow path through which the liquid flows, it is possible to improve the flexibility of the arrangement of the sample storage portion and the flow cell.

BEST MODE FOR CARRYING OUT THE INVENTION

Figure 1:
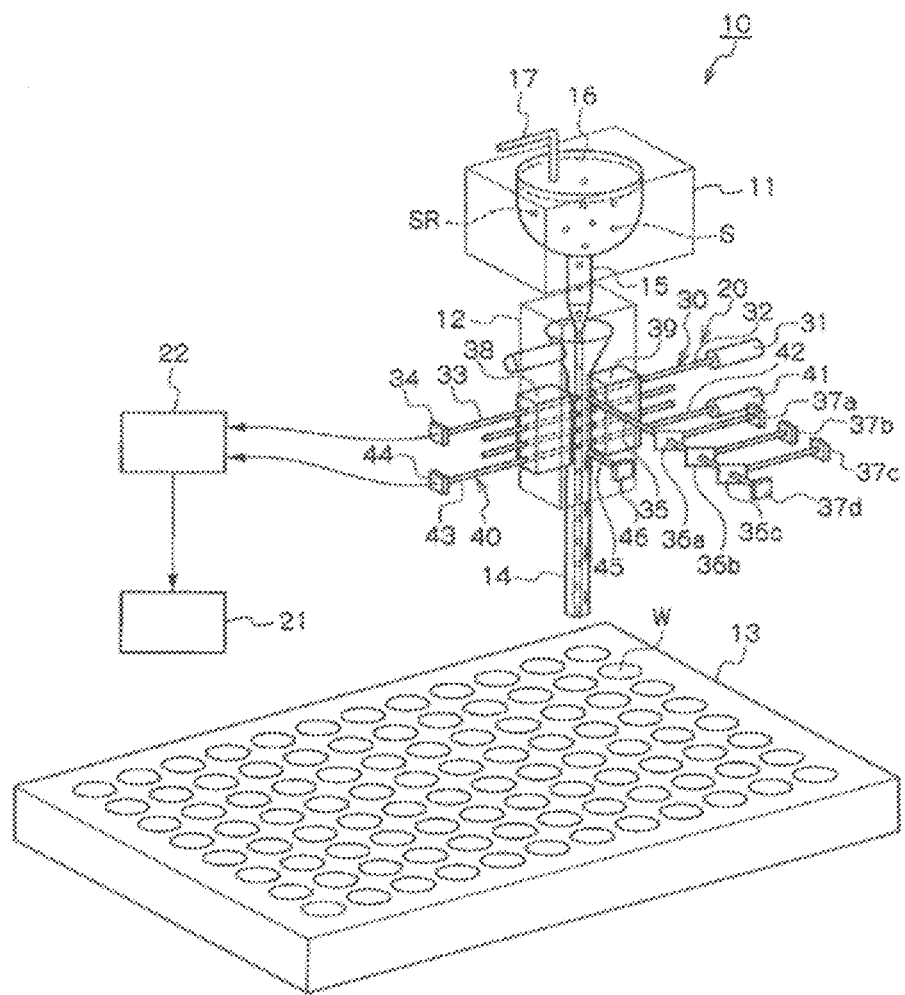
FIG. 1 is a perspective view schematically illustrating the overall structure of a sample identification/sorting apparatus according to a first embodiment of the invention.

Hereinafter, exemplary embodiments of the invention will be described with reference to the accompanying drawings. In the following embodiments, the same components are denoted by the same reference numerals and a description thereof will be omitted.

(First Embodiment)

A sample identification/sorting apparatus 10 according to a first embodiment of the invention will be described with reference to FIGS. 1 to 3.

The sample identification/sorting apparatus 10 irradiates excitation light onto a sample, such as a cell, which is a measurement target dispersed in a liquid flowing through a flow path, to measure optical information of the sample, determines whether the sample needs to be sorted on the basis of the optical information, and sorts a target sample, which is a sorting target, to a collection container on the basis of the determination result. The term "optical information of the sample" means optical information, such as transmission light, side scattered light, and fluorescence from the sample. The term "determining whether the sample needs to be sorted" means determining whether the sample is a target sample, such as a living cell to be sorted, or a non-target sample to be discarded, that is, analyzing the identification of the sample (cell).

Figure 2:
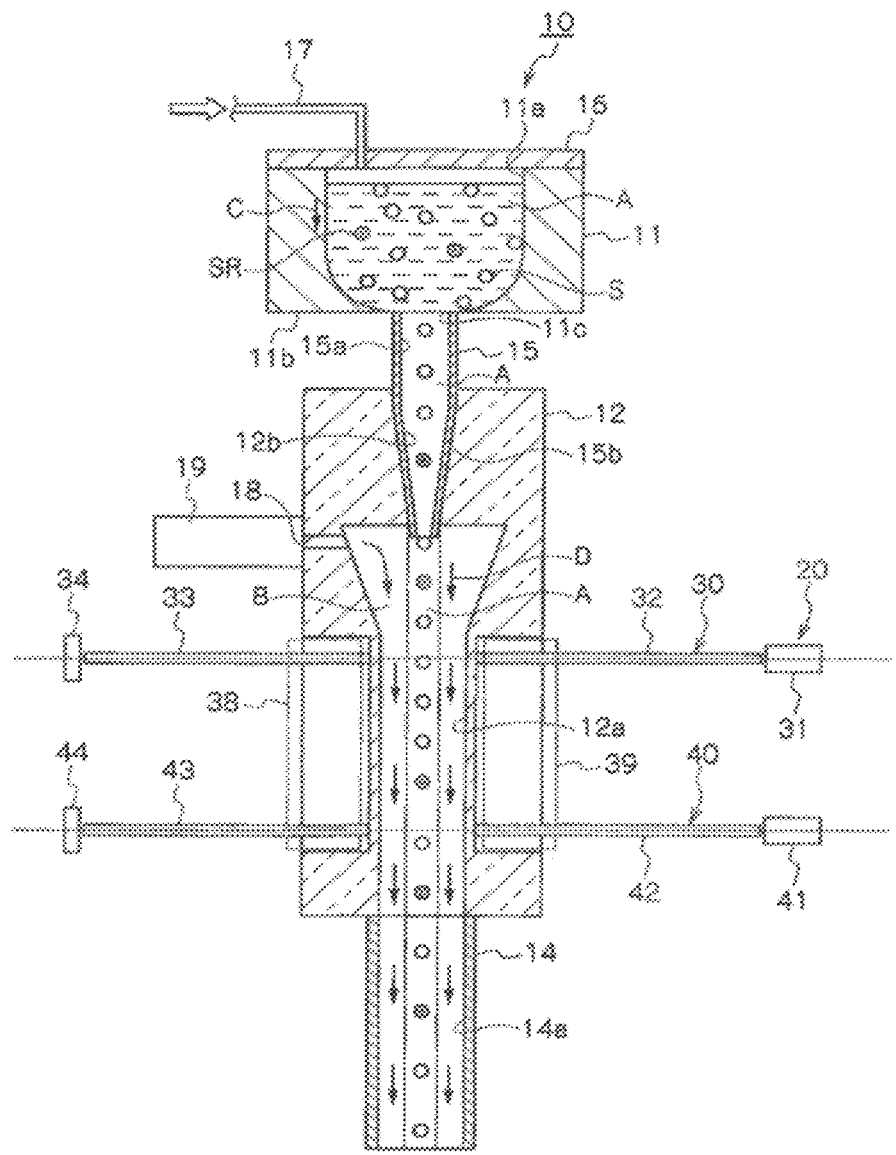
FIG. 2 is an enlarged cross-sectional view illustrating a portion of the sample identification/sorting apparatus shown in FIG. 1 from a sample storage portion to the leading end of a sorting nozzle.
Figure 3:
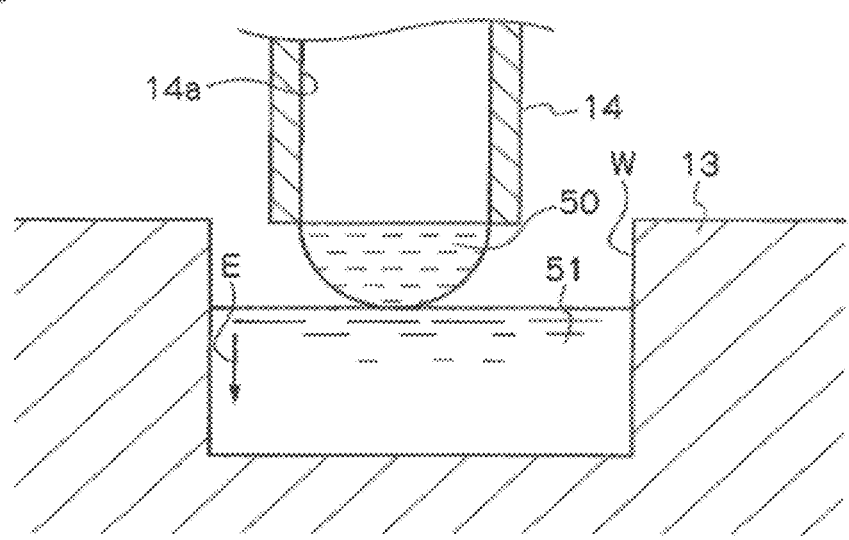
FIG. 3 is a diagram illustrating an example in which the leading end of the sorting nozzle is inserted into a well of a collection container to dispense a solution including a target sample into the well.

In FIGS. 1 and 2, a sample S represented by a white circle is a target sample, such as a living cell to be sorted, and a sample SR represented by a black circle is a non-target sample to be discarded.

As shown in FIGS. 1 and 2, the sample identification/sorting apparatus 10 includes a sample storage portion 11 that stores the samples S and SR dispersed in a liquid A, a flow cell 12 having a flow path 12a through which the liquid A flows, and a sorting nozzle 14 that includes a flow path 14a communicating with the flow path 12a of the flow cell 12 and dispenses a sorting solution including the sample S (target sample) to a culture plate 13 serving as a collection container. The liquid A is a sample suspension obtained by dispersing the samples S and SR in a solution. The flow cell 12 is made of glass or a transparent resin.

The sample identification/sorting apparatus 10 is characterized in that a flow path from the sample storage portion 11 to the leading end of the sorting nozzle 14 is a straight line in order to reduce the damage of a sample, particularly, the damage of a sample, such as a weak cell including an iPS cell.

That is, as shown in FIG. 2, the flow path from the sample storage portion 11 to the leading end of the sorting nozzle 14 is a straight flow path such that the liquid level displacement direction C of the liquid A in the sample storage portion 11 is aligned with the flow direction D of the liquid A in the flow path.

The term "straight flow path" means that the central axis of the flow path from the sample storage portion 11 to the leading end of the sorting nozzle 14 is a straight line. Therefore, for example, the "straight flow path" includes a flow path having a gap in a portion of the wall thereof from the sample storage portion 11 to the leading end of the sorting nozzle 14 and a flow path whose sectional shape is changed as long as the central axes of the flow paths are a straight line.

In addition, the sample identification/sorting apparatus 10 is characterized in that the central axis of the straight flow path is aligned with the vertical direction.

The sample identification/sorting apparatus 10 is also characterized in that the liquid level displacement direction C of the liquid in the sample storage portion 11 is aligned with the flow direction D of the liquid A having the sample dispersed therein in the flow path.

In addition, the sample identification/sorting apparatus 10 is characterized in that the liquid level displacement direction C of the liquid in the sample storage portion 11 is substantially vertical to the liquid level in the collection container (culture plate 13).

The term "liquid level displacement direction in the collection container" means a liquid level displacement direction E in a culture solution 51 (see FIG. 3) in a well W when the culture plate 13 having a plurality of wells W arranged in, for example, a matrix is used as the collection container.

The sample identification/sorting apparatus 10 is characterized in that the collection container (culture plate 13) is disposed below the leading end of the sorting nozzle 14 in the vertical direction when the sample is sorted.

The positional relationship between the culture plate 13 and the sorting nozzle 14 is established "when the sample is sorted."

The culture plate 13 may be disposed at a different position in a standby state and may be moved to below the leading end of the sorting nozzle 14 in the vertical direction when the sample is sorted.

In the standby state, the culture plate 13 may be disposed below the sorting nozzle 14 in the vertical direction or it may be disposed at a position other than below the sorting nozzle 14 in the vertical direction.

As such, in the sample identification/sorting apparatus 10, the following structure is used in order to form a straight flow path from the sample storage portion 11 to the leading end of the sorting nozzle 14.

The sample storage portion 11 is arranged above the flow cell 12. An introduction nozzle 15 having a straight flow path 15a that introduces the liquid A from the sample storage portion 11 to the flow path 12a of the flow cell 12 is provided between the sample storage portion 11 and the flow cell 12.

The sorting nozzle 14 having a straight flow path 14a that introduces the liquid A flowing through the flow path 12a to the well of the culture plate 13 is provided below the flow cell 12.

The sample storage portion 11 is a cup-shaped container in which an opening portion 11a through which the liquid A is introduced is provided at an upper part and a discharge hole 11c is provided in the bottom 11b. That is, the sample storage portion 11 has only the function of a container that stores the samples dispersed in the liquid A.

An openable lid 16 is provided in the sample storage portion 11. A pipe 17 that introduces pressurized air which is adjusted to predetermined pressure into the sample storage portion 11 is provided in the lid 16.

For example, when the sample storage portion 11 is connected to the introduction nozzle 15, the opening portion 11a is opened and the liquid A is introduced into the sample storage portion 11 by, for example, a pipette in order to introduce the liquid A to the sample storage portion 11.

In addition, the sample storage portion 11 may be disconnected from the introduction nozzle 15, the liquid A may be introduced into the sample storage portion 11, and the sample storage portion 11 may be connected to the introduction nozzle 15. In this case, an upper part of the sample storage portion 11 is covered with the lid 16 to prevent the liquid A from being discharged from the discharge hole 11c even when the sample storage portion 11 is disconnected from the introduction nozzle 15.

For example, a disposable syringe (injector) may be used as the sample storage portion 11 and the introduction nozzle 15 may have a syringe structure having a needle with an outside diameter of about 0.70 mm (about 22 G). In this way, an exchangeable product subjected to a sterilizing process may be used. In addition, the leading end of the introduction nozzle 15 is not obliquely cut unlike a general syringe, but it is preferable that the leading end of the introduction nozzle 15 be vertical in the longitudinal direction of the needle.

In addition, it is preferable that the introduction nozzle 15 and the flow cell 12 be filled up with a liquid (sheath liquid) B in advance such that the liquid A does not flow during a predetermined period of time after the liquid A is introduced into the sample storage portion 11. In this case, it is possible to control the liquid A such that the liquid A does not flow by the resistance of the liquid B, that is, pipe resistance acting on the liquid B on the inner wall of the flow path 12a corresponding to the viscosity of the liquid B, until the liquid A and the liquid B are pressurized.

The introduction nozzle 15 is a cylindrical member having a predetermined sectional shape, for example, a circular shape having an inside diameter of about 0.5 mm in a cross-sectional view and includes a tapered portion 15b at a lower part thereof. The upper end of the introduction nozzle 15 is fixed to the bottom 11b of the sample storage portion 11 such that an inlet of the flow path 15a communicates with the discharge hole 11c of the sample storage portion 11. In addition, the tapered portion 15b of the introduction nozzle 15 is fixed to the tapered hole 12b which communicates with the flow path 12a formed at the upper end of the flow cell 12 by pressing force or screws.

In this embodiment, the introduction nozzle 15 is formed separately from the sample storage portion 11 and the flow cell 12. However, the introduction nozzle 15 may be formed integrally with one of the sample storage portion 11 and the flow cell 12. In addition, the introduction nozzle 15 may be formed in a straight line without the tapered portion 15b.

A sheath liquid introduction hole 18 that communicates with the straight flow path 12a and introduces the liquid (sheath liquid) B without any sample to the flow path 12a is provided in the flow cell 12. In addition, a sealing liquid introduction portion 19 for introducing the sheath liquid B adjusted to predetermined pressure to the sheath liquid introduction hole 18 is provided in the flow cell 12.

In the flow path 12a of the flow cell 12, the liquid A is surrounded by the sheath liquid B such that the samples S and SR dispersed in the liquid A flow independently. The flow of the liquid A is referred to as a sample flow, and the flow of the sheath liquid B surrounding the sample flow is referred to as a sheath flow.

The sorting nozzle 14 is fixed to the lower end of the flow cell 12 such that the flow path 12a communicates with the straight flow path 14a. The flow cell 12 and the sorting nozzle 14 may be integrally formed.

As such, the straight flow path 15a of the introduction nozzle 15 communicates with the discharge hole 11c of the sample storage portion 11, the straight flow path 12a of the flow cell 12 communicates with the flow path 15a, and the straight flow path 14a of the sorting nozzle 14 communicates with the flow path 12a. In this way, the flow path from the sample storage portion 11 to the leading end of the sorting nozzle 14 is formed in a straight line. That is, the straight flow path from the sample storage portion 11 to the leading end of the sorting nozzle 14 is formed by the flow path 15a, the flow path 12a, and the flow path 14a.

The sample identification/sorting apparatus 10 is configured such that the sorting nozzle 14 or the culture plate 13 is moved at the time when the sample S reaches the leading end of the sorting nozzle 14 to dispense the sorting solution 50 (FIG. 3) including the sample S to the well W of the culture plate 13. In order to form the structure, as shown in FIGS. 1 and 2, the sample identification/sorting apparatus 10 includes an optical information measuring unit 20 that irradiates excitation light onto the samples S and SR included in the liquid A which flows through the flow path 12a of the flow cell 12 to measure the optical information of the samples, a dispensing unit 21 that moves the sorting nozzle 14 or the culture plate 13 to dispense the sort solution 50 to the culture plate 13, and a control unit 22 that controls the driving of the dispensing unit 21.

The flow path 12a has, for example, a rectangular parallelepiped shape with a size of about 0.1 mm to 0.4 mm×0.1 mm to 0.4 mm.

The sorting nozzle 14 is configured such that the flow path 14a has, for example, a size of about 0.1 mm to 0.4 mm×0.1 mm to 0.4 mm which is equal to that of the flow path 12a and has an inside diameter of about 0.5 mm which is slightly greater than that of the flow path 12a.

That is, when both the flow path 12a of the flow cell 12 and the flow path 14a of the sorting nozzle 14 have a rectangular parallelepiped shape, it is preferable that the minimum side of the flow path 14a≥the maximum side of the flow path 12a be satisfied. Alternatively, when both the flow path 12a of the flow cell 12 and the flow path 14a of the sorting nozzle 14 have a cylindrical shape, it is preferable that the minimum diameter of the flow path 14a≥the maximum diameter of the flow path 12a be satisfied.

As such, since the flow path 14a of the sorting nozzle 14 is greater than the flow path 12a of the flow cell 12 in which the optical information measuring units 20 and 41 are provided, it is possible to reduce the damage of samples, such as living cells flowing through the flow paths 12a and 14a.

As shown in FIGS. 1 and 2, the optical information measuring unit 20 includes two measurement systems 30 and 40 that are provided around the flow path 12a at two different positions in the traveling direction (the flow direction D of the sample flow in the flow path) of the samples S and SR included in the liquid A which flows through the flow path 12a of the flow cell 12. The measurement systems 30 and 40 individually irradiate excitation light onto the sample at different positions in the traveling direction of the sample to measure the optical information of the sample.

The measurement system 30 includes a light irradiating unit that irradiates excitation light onto the sample flowing through the flow path 12a of the flow cell 12, a transmission light receiving unit that receives transmission light, which is the excitation light passing through the sample, and a side scattered light receiving unit that receives side scattered light and fluorescence emitted from the sample.

The light irradiating unit of the measurement system 30 includes a semiconductor laser element 31 that irradiates a laser beam (for example, a beam with a wavelength of 488 nm) with a predetermined wavelength as the excitation light and an optical fiber 32 that transmits the laser beam so as to be irradiated onto the vicinity of the flow (sample flow) of the liquid A passing through the flow path 12*a*. However, the light irradiating unit may be a space coupling optical system without any optical fiber.

The transmission light receiving unit of the measurement system 30 includes an optical fiber 33 that receives the transmission light from the sample in the vicinity of the sample flow and a light receiving element 34 that receives the transmission light propagated through the optical fiber 33.

The side scattered light receiving unit of the measurement system 30 includes an optical fiber 35 that receives the side scattered light from the sample in the vicinity of the sample flow, three optical filters 36*a* to 36*c* that are provided in the optical fiber 35 and separate the side scattered light and fluorescence included in the side scattered light for each wavelength, and four light receiving elements 37*a* to 37*d* that receive light components separated by each optical filter.

The light receiving element 37*a* receives the side scattered light reflected from the optical filter 36*a*. The light receiving element 37*b* receives fluorescence that passes through the optical filter 36*a* and is reflected from the optical filter 36*b*. The light receiving element 37*c* receives fluorescence that passes through the optical filter 36*b* and is reflected from the optical filter 36*c*. The light receiving element 37*d* receives fluorescence passing through the optical filter 36*c*.

The measurement system 40 includes a light irradiating unit that irradiates excitation light onto the sample flowing through the flow path 12*a* of the flow cell 12, a transmission light receiving unit that receives transmission light, which is the excitation light passing through the sample, and a fluorescence receiving unit that receives fluorescence emitted from the sample.

The light irradiating unit of the measurement system 40 includes a semiconductor laser element 41 that irradiates a laser beam (for example, a beam with a wavelength of 635 nm) with a predetermined wavelength as the excitation light and an optical fiber 42 that transmits the laser beam so as to be irradiated onto the vicinity of the sample flow.

The transmission light receiving unit of the measurement system 40 includes an optical fiber 43 that receives the transmission light from the sample in the vicinity of the sample flow and a light receiving element 44 that receives the transmission light propagated through the optical fiber 43.

The optical fibers 32, 33, 35, 42, and 43 of the measurement systems 30 and 40 are held by fiber holding members 38 and 39, and the fiber holding members 38 and 39 are positioned and fixed to the flow cell 12. In this way, the optical fibers are accurately attached to the flow cell 12.

The fluorescence light receiving unit of the measurement system 40 includes an optical fiber 45 that receives fluorescence from the sample in the vicinity of the sample flow and a light receiving element 46 that receives fluorescence propagated through the optical fiber 45.

It is preferable that a photomultiplier tube (PMT) be used as each of the light receiving elements of the measurement systems 30 and 40.

It is preferable that each of the optical fibers be arranged such that a light receiving surface thereof comes into direct contact with the sheath flow.

The side scattered light receiving unit of each of the measurement systems 30 and 40 may receive light using a lens without using the optical fiber.

In addition, the measurement systems 30 and 40 may include a front scattered light receiving unit that receives front scattered light, instead of the transmission light receiving unit.

The dispensing unit 21 includes a stage (not shown) that supports the sorting nozzle 14 or the culture plate 13 such that they can be moved relative to each other and a first motor (not shown) that drives the stage, in order to dispense the sorting solution including the sample S to an arbitrary well W of the culture plate 13.

In addition, the dispensing unit 21 includes a supporting portion that supports a waste tank (not shown) so as to be movable in one direction relative to the sorting nozzle 14 and a second motor that drives the supporting portion.

The control unit 22 determines whether the sample is a target sample (sample S) or a non-target sample (sample SR) on the basis of the optical information (information of transmission light, side scattered light, and fluorescence) obtained by each light receiving unit, that is, the light receiving elements 34, 44, 37*a* to 37*d*, and 46 of the measurement systems 30 and 40. In addition, the control unit 22 measures the flow rate of the samples S and SR on the basis of a difference in the measurement time of the optical information obtained by the light receiving elements 34 and 44 of the measurement systems 30 and 40 and the gap between the light receiving elements 34 and 44, and calculates the time when the samples S and SR reach the leading end of the sorting nozzle 14 on the basis of the measured flow rate.

When it is determined that the sample is the sample S, the control unit 22 controls the driving of the first motor of the dispensing unit 21 at the time when the sample S reaches the leading end of the sorting nozzle 14. In this way, the sorting nozzle 14 or the culture plate 13 is moved such that the leading end of the sorting nozzle 14 is inserted into an arbitrary well W of the culture plate 13 a shown in FIG. 3, and the sort solution 50 including the sample S at the leading end of the sorting nozzle 14 is dispensed to the culture solution 51 in the well W.

When the solution is dispensed, the sorting nozzle 14 may be vibrated such that the sort solution 50 including the sample S at the leading end of the sorting nozzle 14 is dispensed in a droplet shape to the arbitrary well W. In addition, in order to reduce the damage of the sample, it is preferable to use a "non-droplet cell sorting method" that contacts the sort solution 50 with the surface of the culture solution 51 (liquid) in the well W before the sort solution 50 becomes a droplet, as shown in FIG. 3, and dispenses the sort solution 50 to an arbitrary well W, without vibrating the sorting nozzle 14.

The sample identification/sorting apparatus 10 having the above-mentioned structure according to the first embodiment has the following effect and operation.

Since the flow path from the sample storage portion 11 to the leading end of the sorting nozzle 14 is a straight line, there is no curved portion in the flow path through which the liquid A having the sample dispersed therein flows, and the collision risk of a sample, such as a living cell, with the wall of the flow path is reduced. In this way, it is possible to remove or reduce the cause of the damage of the sample, such as a living cell, when the sample is moved from the sample storage portion 11 to the leading end of the sorting nozzle 14 in the straight flow path (sorting process). Therefore, when the cause of the damage of the sample, such as a living cell, in the sorting process is removed or reduced, it is possible to acquire a high-quality living cell. In particular, it is possible to achieve a sample identification/sorting apparatus that is effective in sorting samples, such as weak cells including iPS cells.

Since the flow path from the sample storage portion 11 to the leading end of the sorting nozzle 14 is a straight line such that the liquid level displacement direction C of the liquid A in the sample storage portion 11 is aligned with the flow direction D of the liquid A in the flow path, the size of the apparatus in the horizontal direction is reduced, and the size of the sample identification/sorting apparatus 10 is reduced.

The sample storage portion 11 is provided above the flow cell 12, and the introduction nozzle 15 is provided between the sample storage portion 11 and the flow cell 12. The sorting nozzle 14 is provided below the flow cell 12. As such, since the sample storage portion 11 is provided at the uppermost part, it is possible to set the pressure of pressurized air introduced from the pipe 17 into the sample storage portion 11 to be lower than that in the related art. In this way, it is possible to dispense living cells, particularly, weak cells including iPS cells without any damage and thus reduce the damage of samples such as living cells.

(Second Embodiment)

Next, a sample identification/sorting apparatus 10A according to a second embodiment will be described with reference to FIG. 4.

Figure 4:
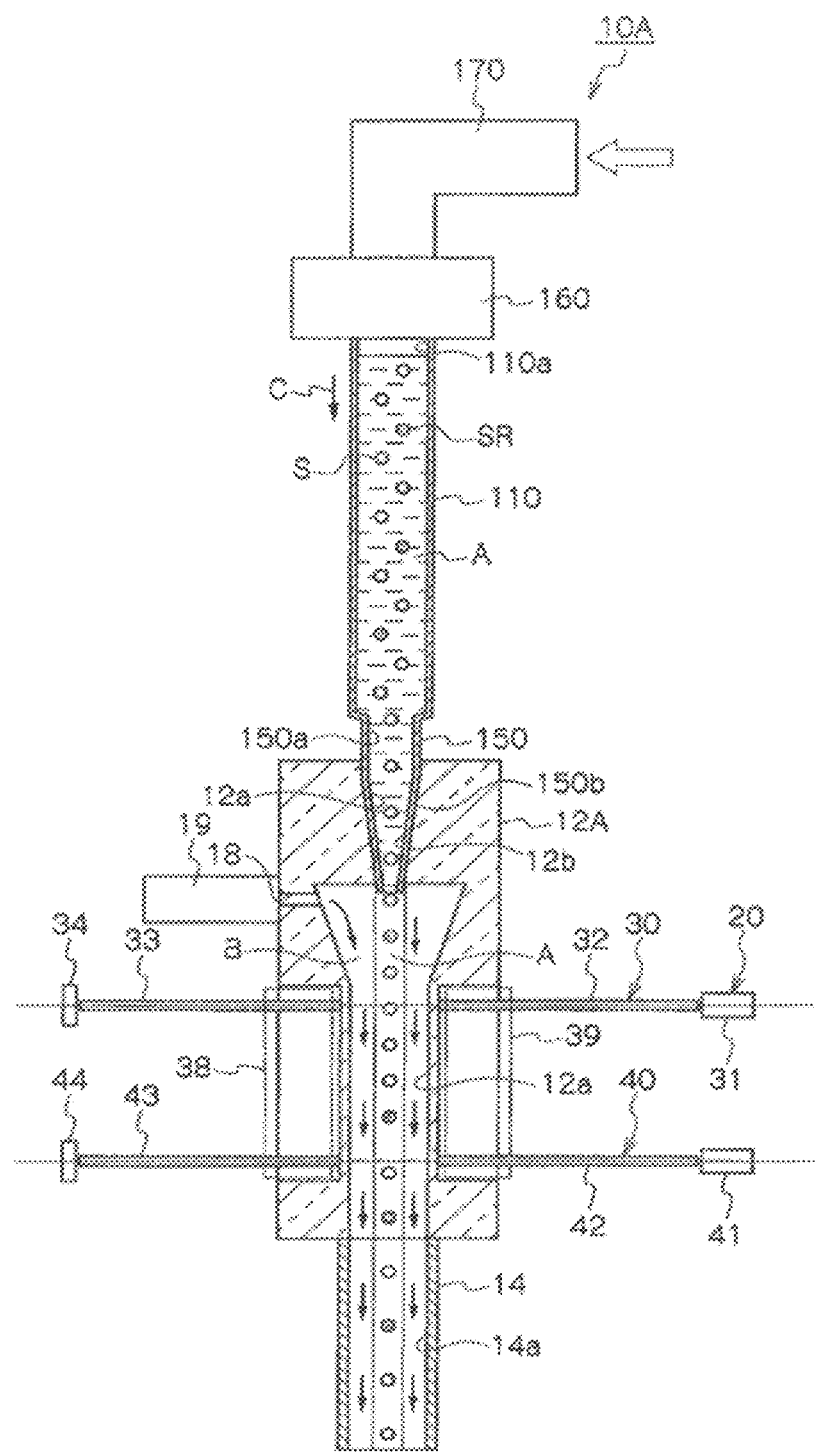
FIG. 4 schematically shows the overall structure of a sample identification/sorting apparatus according to a second embodiment of the invention and is an enlarged cross-sectional view illustrating a portion of the sample identification/sorting apparatus from a sample storage portion to the leading end of a sorting nozzle, similar to FIG. 2.
Figure 5:
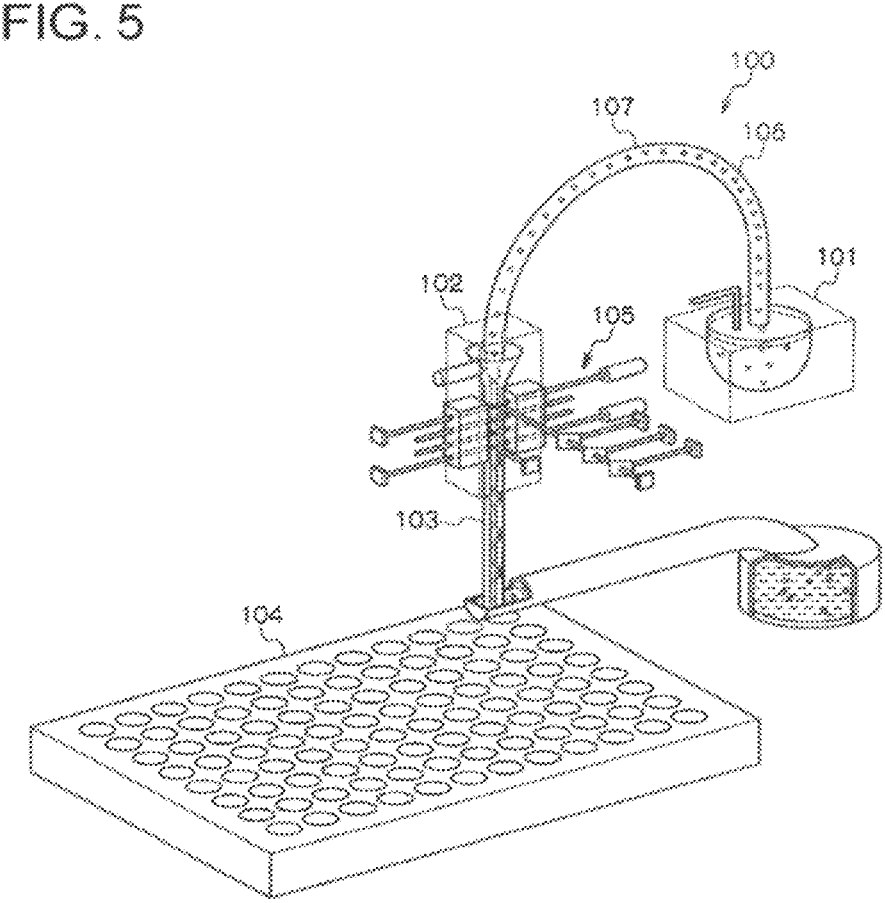
FIG. 5 is a perspective view schematically illustrating the overall structure of a sample identification/sorting apparatus according to the related art.
Figure 6:
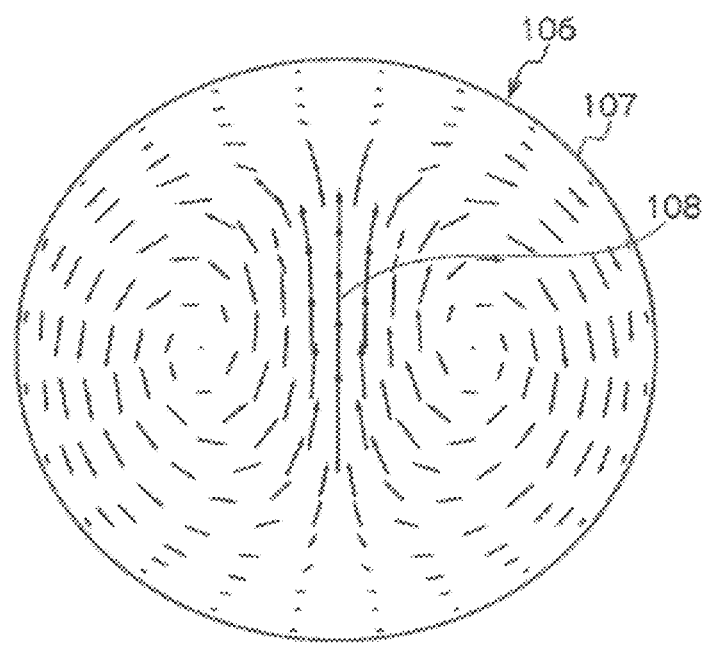
FIG. 6 is a diagram illustrating the flow of a fluid in a flow path of a curved portion in the sample identification/sorting apparatus shown in FIG. 5.

As shown in FIG. 4, the sample identification/sorting apparatus 10A includes a sample storage portion 110 that stores samples S and SR dispersed in a liquid A, a flow cell 12A having a flow path 12a through which the liquid A flows, and a sorting nozzle 14 that includes a flow path 14a communicating with the flow path 12a of the flow cell 12A and dispenses a sorting solution including the target sample S to a culture plate 13.

The sample storage portion 110 is a tubal container in which an opening portion 110a through which the liquid A is introduced is provided at an upper part and a discharge hole from which the liquid A is discharged is provided at a lower part. An openable lid 160 is provided in the sample storage portion 110. A pipe 170 that introduces pressurized air which is adjusted to predetermined pressure into the sample storage portion 110 is provided in the lid 160.

An introduction nozzle 150 having a straight flow path 150a that introduces the liquid A from the sample storage portion 110 to the flow path 12a of the flow cell 12A is provided between the sample storage portion 110 and the flow cell 12.

The introduction nozzle 150 is fixed to the lower end of the tubal sample storage portion 110. The introduction nozzle 150 may be formed integrally with the tubal sample storage portion 110. A tapered portion 150b is formed at the lower end of the introduction nozzle 150.

When the sample identification/sorting apparatus 10A is used, the tapered portion 150b of the introduction nozzle 150 is inserted into a tapered hole 12b of the flow cell 12 to fix the introduction nozzle 150 to the flow cell 12A.

The tubal sample storage portion 110 and the introduction nozzle 150 may be cylindrical pipes having the same inside diameter and outward appearance. For example, the tubal sample storage portion 110 and the introduction nozzle 150 may be disposable syringes (injectors).

In the sample identification/sorting apparatus 10A, the flow path from the sample storage portion 110 to the leading end of the sorting nozzle 14 is also a straight line in order to reduce the damage of samples, particularly, the damage of samples, such as weak cells including iPS cells. That is, as shown in FIG. 4, the flow path from the sample storage portion 110 to the leading end of the sorting nozzle 14 is a straight line such that the liquid level displacement direction C of the liquid A in the sample storage portion 110 is aligned with the flow direction D of the liquid A in the flow path.

As such, in the sample identification/sorting apparatus 10A according to this embodiment, the flow path from the introduction nozzle 150 to the sorting nozzle 14 is a straight line.

In the sample identification/sorting apparatus 10A, the inside of the sample storage portion 110 communicates with the straight flow path 150a of the introduction nozzle 150, the straight flow path 12a of the flow cell 12A communicates with the flow path 150a, and the straight flow path 14a of the sorting nozzle 14 communicates with the flow path 12a. In this way, the flow path from the sample storage portion 110 to the leading end of the sorting nozzle 14 is a straight line. That is, the straight flow path from the sample storage portion 110 to the leading end of the sorting nozzle 14 is formed by the flow path 150a, the flow path 12a, and the flow path 14a.

The other structures of the sample identification/sorting apparatus 10A are the same as those of the sample identification/sorting apparatus 10 shown in FIGS. 1 and 2.

According to the sample identification/sorting apparatus 10A, since the flow path from the tubal sample storage portion 110 to the leading end of the sorting nozzle 14 is a straight line, there is no curved portion in the flow path through which the liquid A having samples dispersed therein flows, and the collision risk of the sample, such as a living cell, with the wall of the flow path is reduced. In this way, it is possible to remove or reduce the cause of the damage of the sample, such as a living cell, when the sample is moved from the sample storage portion 110 to the leading end of the sorting nozzle 14 in the straight flow path. Therefore, it is possible to acquire a high-quality living cell. In particular, when samples, such as weak cells including iPS cells, are sorted, it is possible to acquire high-quality living cells.

(Sample Identification/Sorting Method)

Next, a sample identification/sorting method according to an embodiment of the invention will be described.

The sample identification/sorting method irradiates light onto samples (samples S and SR shown in FIG. 2), which are measurement targets dispersed in a liquid (the liquid A shown in FIG. 2) flowing through the flow path, to measure the optical information of the samples, determines whether the samples need to be sorted on the basis of the optical information, and sorts a target sample (sample S), which is a sorting target, to the collection container on the basis of the determination result.

The sample identification/sorting method is characterized in that it makes the samples S and SR dispersed in the liquid A flow through a straight flow path from the sample storage portion (for example, the sample storage portion 11 shown in FIG. 2) storing the samples and dispenses a target sample to the collection container.

For example, as shown in FIG. 2, the straight flow path from the sample storage portion 11 to the leading end of the sorting nozzle 14 is formed by the flow path 15a, the flow path 12a, and the flow path 14a.

In the sample identification/sorting method, a sorting solution including a target sample is dispensed to the collection container (the culture plate 13 shown in FIG. 2) at the time when the target sample reaches the leading end of the straight flow path (for example, the leading end of the sorting nozzle 14 shown in FIGS. 1 and 2).

In addition, the sample identification/sorting method is characterized in that the liquid level displacement direction of the liquid in the sample storage portion (for example, the liquid level displacement direction C of the liquid A in the sample storage portion 11 shown in FIG. 2) is aligned with the flow direction D of the liquid A in the flow path.

The sample identification/sorting method is also characterized in that the sample dispersed in the liquid A is moved in a straight line from the sample storage portion (for example, the sample storage portion 11) and is sorted to the culture plate 13 serving as a collection container.

According to the sample identification/sorting method, the samples S and SR dispersed in the liquid A flow through the straight flow path from the sample storage portion storing the samples and a target sample is dispersed to the collection container. Therefore, there is no curved portion in the flow path through which the liquid A having samples dispersed therein flows, and the collision risk of the samples, such as living cells, with the wall of the flow path is reduced. In this way, it is possible to remove or reduce the cause of the damage of the samples, such as living cells, when the samples are moved through the straight flow path. Therefore, it is possible to acquire high-quality living cells. In particular, when samples, such as weak cells including iPS cells, are sorted, it is possible to acquire high-quality living cells.

(Third Embodiment)

Figure 7:
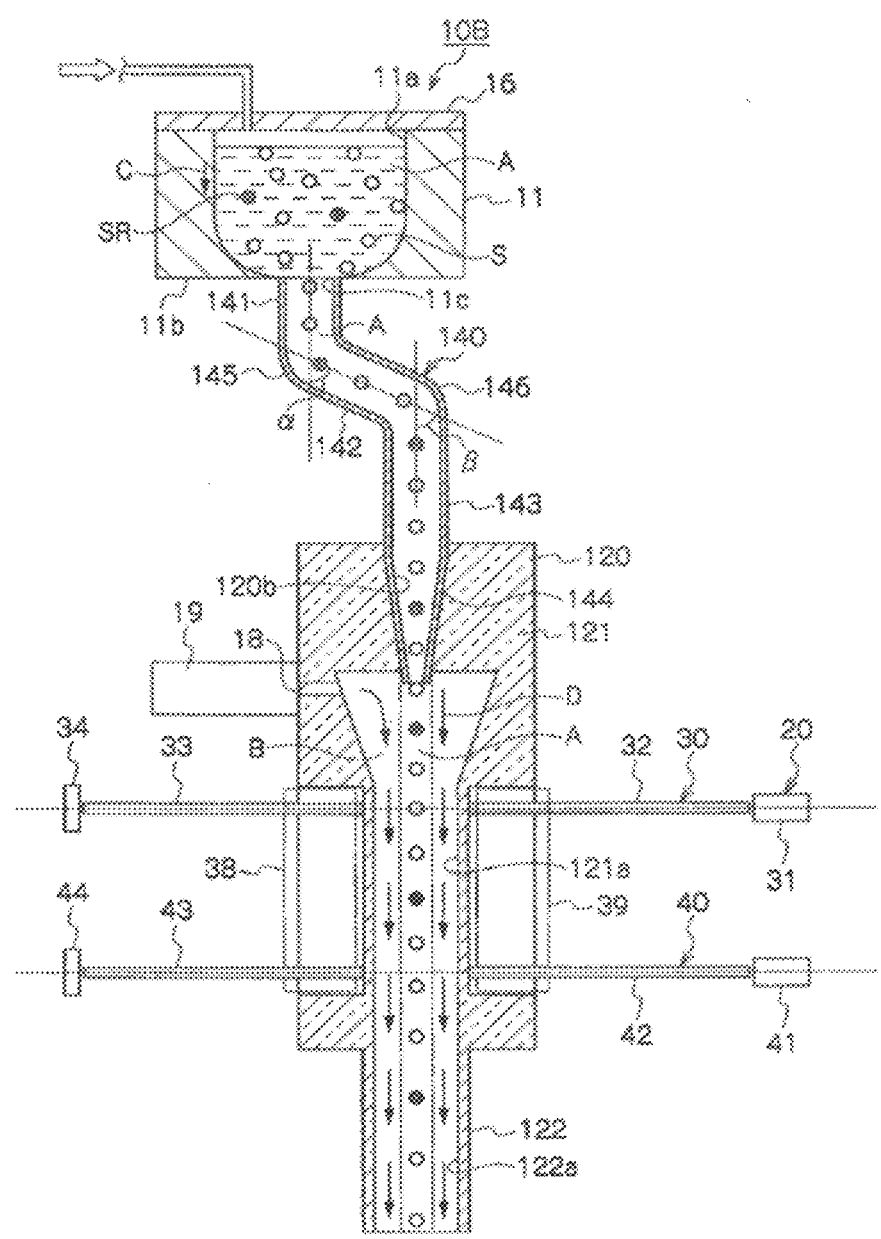
FIG. 7 is a cross-sectional view schematically illustrating the overall structure of a sample identification/sorting apparatus according to a third embodiment of the invention, similar to FIG. 2.

Next, a sample identification/sorting apparatus 10B according to a third embodiment will be described with reference to FIG. 7.

The sample identification/sorting apparatus 10B is characterized in that it includes two bent portions 145 and 146 each of which changes the flow direction of a liquid A at an angle of less than 90 degrees in a flow path.

Specifically, in the sample identification and dispersing apparatus 10B, an introduction nozzle 140 including the two bent portions 145 and 146 is used as a nozzle that introduces the liquid A from the sample storage portion 11 to a flow path 121a of a flow cell 120, instead of the introduction nozzle 15 of the sample identification/sorting apparatus 10 shown in FIG. 2.

The introduction nozzle 140 includes straight pipe portions 141, 142, and 143, the bent portions 145 and 146, and a tapered portion 144. The straight pipe portion 141 is connected to a discharge hole 11c of the sample storage portion 11, and the tapered portion 144 is connected to a tapered portion 120b of the flow cell 120. Each of the angle α of the bent portion 145 and the angle β of the bent portion 146 is formed such that the flow direction of the liquid in the flow path is changed at an angle of less than 90 degrees. In this example, the angles α and β are, for example, 60 degrees.

When each of the angles (α and β) of the bent portions 145 and 146 is more than 90 degrees, there is a concern that the sample dispersed in the liquid A will deviate from the flow direction of the liquid A in the flow path due to the secondary flow of the liquid A generated by centrifugal force and inertia, contact the inner wall of the introduction nozzle (the wall of the flow path), and be damaged. Therefore, it is preferable that each of the angles (α and β) of the bent portions 145 and 146 be less than 90 degrees. In addition, it is preferable that the angles (α and β) be as small as possible.

In addition, the sample identification/sorting apparatus 10B is characterized in that a sorting nozzle portion 122 having a flow path 122a is formed integrally with a flow cell main portion 121 of the flow cell 120.

As in the sample identification/sorting apparatus 10B according to this embodiment, when the introduction nozzle 140 including the bent portions 145 and 146 is used, the flow path from the flow cell 120 to the sorting nozzle portion (sorting nozzle) 122 is a straight line.

The other structures are the same as those of the sample identification/sorting apparatus 10 shown in FIG. 2.

According to the sample identification/sorting apparatus 10B having the above-mentioned structure, the introduction nozzle 140 including the two bent portions 145 and 146 which are formed such that the flow direction of the liquid A in the flow path is changed at an angle of less than 90 degrees is used as the nozzle that introduces the liquid A from the sample storage portion 11 to the flow path 121a of the flow cell 120. In this way, it is possible to reduce the possibility that the sample dispersed in the liquid A will deviate from the flow direction of the liquid A in the flow path due to the secondary flow of the liquid A generated by centrifugal force and inertia, contact the inner wall of the introduction nozzle 140 (the wall of the flow path), and be damaged.

In addition, since the introduction nozzle 140 including the two bent portions 145 and 146 is used as the nozzle that introduces the liquid A from the sample storage portion 11 to the flow path 121a of the flow cell 120, it is possible to offset the center (the center in the vertical direction) of the sample storage portion 11 from the center (the center in the vertical direction) of the flow cell 120. Therefore, even when there are restrictions in the arrangement of the sample storage portion 11 and the flow cell 120 such that the centers thereof are not aligned with each other, it is possible to improve the flexibility of the arrangement of the sample storage portion and the flow cell and thus improve the flexibility of the design.

Since the sorting nozzle portion 122 having the flow path 122a is formed integrally with the flow cell main portion 121 of the flow cell 120, it is possible to form a structure in which there is no gap in the inner wall of the flow path and reduce a component cost and an assembly cost.

In the sample identification/sorting apparatus 10B, the bent portions 145 and 146 formed such that the flow direction of the liquid A in the flow path is changed at an angle of less than 90 degrees are provided in the introduction nozzle 140 that introduces the liquid A from the sample storage portion 11 to the flow path 121a of the flow cell 120, but the invention is not limited thereto. One bent portion or three or more bent portions formed such that the flow direction of the liquid A in the flow path is changed at an angle of less than 90 degrees may be provided in the flow path of the sorting nozzle portion 122.

In addition, in the sample identification/sorting apparatus 10B, the two bent portions 145 and 146 are provided in the introduction nozzle 140, but the invention can be applied to a structure in which one bent portion or three or more bent portions are provided in the introduction nozzle 140 such that the flow direction of the liquid A in the flow path is changed at an angle of less than 90 degrees. For example, one bent portion may be provided in the introduction nozzle 140 such that the flow direction of the liquid A in the flow path is changed at an angle of less than 90 degrees. That is, the invention can be widely applied to a sample identification/sorting apparatus in which the difference between the flow direction of the liquid A in the flow path at the outlet (discharge hole 11 C) of the sample storage portion 11 and the flow direction of the liquid A in the flow path at the leading end of the sorting nozzle (the sorting nozzle 14 shown in FIG. 2 or the sorting nozzle portion 122 shown in FIG. 7) is less than 90 degrees.

In addition, the invention can be widely applied to a sample identification/sorting apparatus in which the difference between the liquid level displacement direction of the liquid in the sample storage portion and the flow direction of the liquid having samples dispersed therein in the flow path is less than 90 degrees.

The sample identification/sorting apparatus and the sample identification/sorting method according to the invention can be applied to various fields in which genes, immune systems, and biopolymers, such as proteins, amino acids, and sugars, need to be examined, analyzed, and assayed, such as an engineering field, an agricultural field including, for example, food, agriculture, and seafood processing, a pharmaceutical field, a medical field including, for example, sanitation, health, immunization, disease, and genetics, and a science field including chemicals and biology.

DESCRIPTION OF REFERENCE NUMERALS AND SIGNS 10, 10A, 10B: SAMPLE IDENTIFICATION/SORTING APPARATUS
11, 110: SAMPLE STORAGE PORTION
11a: OPENING PORTION
11b: BOTTOM
11c: DISCHARGE HOLE
12, 12A, 120: FLOW CELL
12a, 121a: FLOW PATH
13: CULTURE PLATE (COLLECTION CONTAINER)
14: SORTING NOZZLE
14a: FLOW PATH
15, 150: INTRODUCTION NOZZLE
15a, 150a: FLOW PATH
20: OPTICAL INFORMATION MEASURING UNIT
21: DISPENSING UNIT
22: CONTROL UNIT
30, 40: MEASUREMENT SYSTEM
122: SORTING NOZZLE PORTION
122a: FLOW PATH
140: INTRODUCTION NOZZLE
145, 146: BENT PORTION
A: LIQUID
B: SHEATH LIQUID B
S: SAMPLE (TARGET SAMPLE)
SR: SAMPLE (NON-TARGET SAMPLE)

The invention claimed is:

1. A sample identification/sorting apparatus that irradiates light onto a sample, which is a measurement target dispersed in a liquid flowing through a flow path, to measure optical information of the sample, determine whether the sample needs to be sorted on the basis of the optical information, and sort out a target sample, which is a sorting target, to a collection container on the basis of a determination result, comprising:
    a sample storage portion storing the sample dispersed in the liquid;
    a flow ell including a first flow path through which the liquid flows and an optical information measuring unit which measures the optical information of the sample;
    a sorting nozzle including a second flow path which communicates with the first flow path of the flow cell and dispenses a sorting solution containing the target sample therein to the collection container;
    a sealing liquid introduction portion which supplies sheath liquid to the first flow path of the flow cell such that the sheath liquid surrounds the liquid in a tubular manner; and
    an introduction nozzle including a third flow path which introduces the liquid from the sample storage portion to the first flow path of the flow cell,
    wherein the second flow path has one exit without branching,
    wherein a difference between a flow direction of the liquid at an outlet of the sample storage portion and a flow direction of the liquid at a leading end of the sorting nozzle is less than 90 degrees, and
    wherein the liquid that is surrounded by the sheath liquid in the first and second flow paths from the flow cell to the sorting nozzle flows along a straight line within a cylindrical space.

2. The sample identification/sorting apparatus according to claim 1,
    wherein a flow direction of the liquid in the first and second flow paths extending from the sample storage portion, through which the fluid flows, to the leading end of the sorting nozzle is changed at an angle of less than 90 degrees.

3. The sample identification/sorting apparatus according to claim 1,
    wherein the first and second flow paths from the flow cell to the sorting nozzle form a straight line.

4. The sample identification/sorting apparatus according to claim 1,
    wherein the sorting nozzle or the collection container is moved to dispense the sorting solution to the collection container at the time when the target sample reaches the leading end of the sorting nozzle.

5. The sample identification/sorting apparatus according to claim 1,
    wherein a central axis of the first and second flow paths is aligned with a vertical direction.

6. The sample identification/sorting apparatus according to claim 1,
    wherein a difference between a liquid level displacement direction of the liquid in the sample storage portion and a flow direction of the liquid having the sample dispersed therein in the first and second flow paths is less than 90 degrees.

7. The sample identification/sorting apparatus according to claim 1,
    wherein a liquid level displacement direction of the liquid in the sample storage portion is aligned with a flow direction of the liquid having the sample dispersed therein in the first flow path.

8. The sample identification/sorting apparatus according to claim 1,
    wherein the collection container is disposed below the leading end of the sorting nozzle in a vertical direction when the sample is sorted.

9. The sample identification/sorting apparatus according to claim 1,
    wherein a liquid level displacement direction of the sample storage portion is substantially vertical to a level of the liquid in the collection container.

10. The sample identification/sorting apparatus according to claim 1,
    wherein the sample storage portion is arranged above the flow cell,
    the sample storage portion is a cup-shaped container in which an opening portion through which the liquid is introduced is provided at an upper part and. a discharge hole is provided in the bottom, and
    the introduction nozzle including the third flow path that introduces the liquid from the sample storage portion to the first flow path of the flow cell is provided between the sample storage portion and the flow cell.

11. The sample identification/sorting apparatus according to claim 1,
wherein the sample storage portion is arranged above he flow cell, and
the sample storage portion is a tubal container that includes an opening portion through which the liquid is introduced at an upper part thereof and has a function of storing the sample and a function as a fourth flow path which forms a portion of the first flow path and introduces the liquid to the flow path of the flow cell.

12. A sample identification/sorting apparatus that dispenses a target sample to a collection container, comprising:
an optical information measuring unit that irradiates light onto a sample, which is a measurement target dispersed in a liquid flowing through a flow path, to measure optical information of the sample;
a dispensing unit that dispenses a sorting solution including the target sample therein, which is a sorting target, to the collection container;
a control unit that determines whether the sample needs to be sorted on the basis of the optical information and controls driving of the dispensing unit on the basis of determination result;
a sample storage portion that stores the sample dispersed in the liquid;
a flow cell including a first flow path through which the liquid flows and the optical information measuring unit that measures the optical information of the sample; and
a sorting nozzle that includes a second flow path communicating with the first flow path of the flow cell and dispenses the sorting solution including the target sample to the collection container;
a sealing liquid introduction portion which supplies sheath liquid to the first flow path of the flow cell such that the sheath liquid surrounds the liquid in a tubular manner; and
an introduction nozzle including a third flow path which introduces the liquid from the sample storage portion to the first flow path of the flow cell,
wherein the second flow path has one exit without branching,
wherein a difference between a flow direction of the liquid at an outlet of the sample storage portion and a flow direction of the liquid at the leading end of the sorting nozzle is less than 90 degrees, and
wherein the liquid that is surrounded by the sheath liquid in the first and second flow paths from the flow cell to the sorting nozzle flows along a straight line within a cylindrical space with a constant diameter.

13. The sample identification/sorting apparatus according to claim 12,
wherein the optical information measuring unit includes a plurality of measurement systems that are provided around the first flow path at two or more different positions in the traveling direction of the sample and measure the optical information, and
the control unit identifies whether the sample is a target sample or a non-target sample on the basis of optical information obtained by the plurality of measurement systems, measures the flow rate of the target sample on the basis of a difference in the measurement time of the optical information obtained by the plurality of measurement systems and a gap between the measurement systems in the traveling direction of the sample, calculates the time when the target sample reaches the leading end of the sorting nozzle, and controls the driving of the dispensing unit at the time when the target sample reaches the leading end of the sorting nozzle.

14. The sample identification/sorting apparatus according to claim 1,
wherein the sheath liquid does not include the sample.

15. A method of identifying and sorting a sample by irradiating light onto the sample, which is a measurement target dispersed in a liquid flowing through a flow path, to measure the optical information of the sample, determining whether the sample needs to be sorted on the basis of the optical information, and sorting the target sample, which is a sorting target, to the collection container on the basis of a determination result, the method comprising:
storing the sample dispersed in a liquid in a sample storage portion;
causing the liquid to flow through a first flow path of a flow cell and measuring the optical information of the sample by an optical information measuring unit;
dispensing a sorting solution including a target sample to a collection container from a sorting nozzle that includes a second flow path that communicates with the first flow path of the flow cell;
introducing the liquid from the sample storage portion to the first flow path of the flow cell by a third flow path of an introduction; and
supplying a sheath liquid to the first flow path of the first cell such that the sheath liquid surrounds the liquid in a tubular manner,
wherein the second flow path has one exit without branching,
wherein a difference between a flow direction of the liquid at an outlet of the sample storage portion and a flow direction of the liquid at the leading end of the sorting nozzle is less than 90 degrees,
wherein the flow direction of the liquid in the first, second, and third flow paths from the sample storage portion to the leading end of the sorting nozzle is changed at an angle of less than 90 degrees,
wherein the sample identification/sorting apparatus further includes an introduction nozzle including the third flow path that introduces the liquid from the sample storage portion to the first flow path of the flow cell, and
wherein the liquid that is surrounded by the sheath liquid in the first and second flow paths from the flow cell to the sorting nozzle flows along a straight line within a cylindrical space with a constant diameter.

16. The method of identifying and sorting a sample according to any claim 15,
wherein the sort solution is dispensed to the collection container at the time when the target sample reaches the leading end of the first and second flow paths.

17. The method of identifying and sorting a sample according to claim 15,
wherein the flow direction of the liquid having the sample dispersed therein in the first and second flow paths is aligned with a vertical direction.

18. The method of identifying and sorting a sample according to claim 15,
wherein the liquid level displacement direction of the liquid in the sample storage portion is aligned with a flow direction of the liquid in the first and second flow paths.

19. The method of identifying and sorting a sample according to claim 15, wherein the sample dispersed in the liquid is moved in a straight line from the sample storage portion and is sorted to the collection container.

20. The sample identification/sorting apparatus according to claim 1,
wherein at least one bent portion is provided such that a flow direction of the liquid is changed at an angle of less than 90 degrees.

21. The sample identification/sorting apparatus according to claim 20,
wherein the sort solution including the target sample at the leading end of the sorting nozzle comes into contact with a liquid in the collection container to be dispensed to the collection container, thereby sorting the target sample.

22. The sample identification/sorting apparatus according to claim 20,
wherein a size of the second flow path of the sorting nozzle is equal to or greater than of the first flow path of the flow cell.

* * * * *